United States Patent [19]

Takemoto et al.

[11] 4,144,882
[45] Mar. 20, 1979

[54] DEVICE FOR EXPOSING TEETH TO RADIATION OF ULTRASONIC WAVES

[75] Inventors: Kiyochika Takemoto, Kodaira; Yasuo Suzuki, Higashi Kurume; Yoshihito Ochiai, Fujisawa; Syozi Nakashima, Ninomiya; Midori Hayashi, Yamakita, all of Japan

[73] Assignee: Lion Hamigaki Kabushiki Kaisha, Japan

[21] Appl. No.: 751,270

[22] Filed: Dec. 17, 1976

[30] Foreign Application Priority Data

Dec. 20, 1975 [JP] Japan ................................ 50-152209

[51] Int. Cl.² ............................................. A61M 31/00
[52] U.S. Cl. ................................ 128/172.1; 32/40 R; 32/DIG. 4
[58] Field of Search ................ 128/172.1, 24 A, 62 A, 128/409; 32/40 R, DIG. 4

[56] References Cited
U.S. PATENT DOCUMENTS 3,371,660  3/1968  Carlin ........................... 128/24 A X
3,380,446  4/1968  Martin ......................... 128/172.1 X
3,401,690  9/1968  Martin .............................. 128/172.1

Primary Examiner—Lee S. Cohen
Attorney, Agent, or Firm—Steinberg & Blake

[57] ABSTRACT

A device for exposing teeth to radiation of ultrasonic waves while the teeth are contacted by a decay-retarding agent, for forming a reinforcing layer of the latter agent on the teeth. In addition to a generator for generating ultrasonic waves, the device includes a support structure which carries a plate capable of transmitting and reflecting the ultrasonic waves. The latter plate is situated between the generator and teeth toward which waves are generally directed from the generator, so that the latter waves are received by this plate which transmits part of the waves through the plate to the teeth at the side of the plate opposite from the generator while another part of the waves are reflected by this plate away from the teeth which receive the transmitted waves, so that in this way the reflected waves may be utilized to treat additional teeth.

15 Claims, 14 Drawing Figures (a)

(b)

DEVICE FOR EXPOSING TEETH TO RADIATION OF ULTRASONIC WAVES

BACKGROUND OF THE INVENTION

The present invention relates to a device for forming a reinforcing layer of a tooth decay-retarding agent on the surface of a tooth by exposing the tooth to ultrasonic waves in the presence of the tooth decay-retarding agent through a ultrasonic wave transmitting medium.

In order to retard tooth decay, it is known to coat manually the surface of the tooth with a tooth decay-retarding agent such as tin fluoride, sodium fluoride or fluoroamine. However, if reliance is made only on such a coating to retard tooth decay, the results are not satisfactory inasmuch as such a coating has only a poor capability of adhering to a tooth and is dissolved away in a relatively short time. Thus, with such procedures it is impossible to achieve a lasting effect for the tooth decay-retarding agent. Furthermore, even while a coating of a tooth decay-retarding agent remains at the surface of a tooth, the capability of preventing calcium from dissolving out from the tooth surface is extremely poor.

It has already been proposed by some of use to treat teeth in such a way that ultrasonic waves are applied to a surface of a tooth which is contacted by a decay-retarding agent so as to form a reinforcing covering layer of the decay-retarding agent on the surface of the tooth. Excellent results are achieved by such a procedure with respect to preventing dissolving-out of calcium and reinforcing the tooth surface by strengthening the same.

Since this method for forming a reinforcing layer on the surface portion of a tooth by radiation of ultrasonic waves in the presence of a tooth decay-retarding agent is based on the novel finding, an apparatus or device for practising this method effectively is not known in the art.

When a ultrasonic vibrator utilizing, for example, vertical vibrations is used for practising the above treatment method, an excessive sonic pressure is applied to the surface of a front tooth and a pain is often given to a patient, and ultrasonic waves of a sufficient sonic pressure are not transmitted to the back side of a tooth or to a grinding tooth. Accordingly, it is often difficult to perform the treatment uniformly. When ultrasonic waves are applied in the presence of a tooth decay-retarding agent, a higher treatment effect can be attained if the ultrasonic waves applied have a relatively low frequency, namely 500 KHz or lower. In order to obtain ultrasonic waves having a low frequency, dimensions of an oscillating member must be enlarged. If a large oscillating member is used, the treatment in the oral cavity becomes difficult or often impossible. Furthermore, since vertical vibrations are utilized, a number of vibrators must be used when a broad range of teeth in the oral cavity are treated at one time.

SUMMARY OF THE INVENTION

It is therefore a primary object of the present invention to provide a device for forming a reinforcing layer of a tooth decay-retarding agent on the surface of a tooth by radiation of ultrasonic waves in the presence of the tooth decay-retarding agent, wherein by arranging a reflecting plate capable of reflecting a part of ultrasonic waves and allowing another part of ultrasonic waves to pass therethrough in a ultrasonic wave transmitting passage to partially change the direction of the ultrasonic waves, the foregoing defects involved in the conventional means can be overcome, generation of heat by excessive local radiation of ultrasonic waves on some teeth can be prevented and not only front surfaces of front teeth but also the back faces of the teeth and even grinding teeth can be treated with ease substantially uniformly, and wherein even if a small number of vibrators (even one vibrator will do) are used for the treatment, a relatively broad range of teeth can be treated and even if ultrasonic waves having a relatively low frequency is used, the interior of the oral cavity can easily be exposed to the ultrasonic waves assuredly.

In accordance with the present invention, the foregoing and other objects and advantages can be attained by a device for forming a reinforcing layer of a tooth decay-retarding agent on the surface portion of a tooth by radiation of ultrasonic waves to the surface of the tooth in the presence of the tooth decay-retarding agent, which comprises a reflecting plate for reflecting ultrasonic waves emitted from a ultrasonic wave generator, said reflecting plate being capable of reflecting a part of the ultrasonic waves and allowing another part of the ultrasonic waves to pass therethrough and said reflecting plate being disposed at a certain angle to the radiation direction of the ultrasonic waves.

BRIEF DESCRIPTION OF THE DRAWINGS

The drawings illustrate embodiments of the present invention, in which:

FIG. 13-(b) is a graph illustrating results (Vickers hardness) of the experiment shown in FIG. 13-(a).

DETAILED DESCRIPTION OF THE PREFERRED EMBODIMENTS

Figure 1:
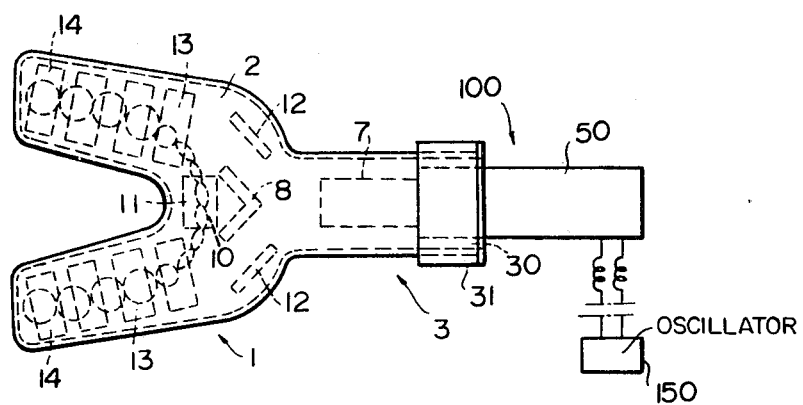
FIG. 1 is a plan view showing an embodiment of the device of the present invention which includes a tray.

Embodiments of the device of the present invention will now be described in detail by reference to the accompanying drawings.

Referring now to FIGS. 1 to 6, a tray 2 embodying the device of the present invention comprises a horseshoe portion 1 and a handle portion 3 attached thereto, and this tray 2 is formed to have a shape covering one of the upper and lower tooth row entirely. The tooth-covering portion of the tray 2 is formed as a U-shaped groove 5. Both the horseshoe portion 1 and handle portion 3 of the tray 2 have a hollow structure, and the hollow portions are connected to each other to form a hollow portion 6 of the tray 2 in which a ultrasonic wave transmitting medium can be contained. In the drawings, reference numeral 4 represents a tooth.

A horn 7 of a ultrasonic wave generator 100 which is vibrated by a magnetostriction vibrator to radiate vertical ultrasonic waves is clamped and fixed to the handle portion 3 by a clamping ring 31 through a packing 30 attached to a casing 50 of the ultrasonic wave generator 100 and the inner wall face of the handle portion 3.

The tray 2 is composed of a material allowing transmission of ultrasonic waves but not allowing permeation of the ultrasonic wave transmitting medium in the hollow portion 6, such as plastics, aluminum foils and stainless steel thin plates. As the ultrasonic wave transmitting medium contained in the hollow portion 6 of the tray 2, there can be used fluids except gases, for example, oils such as silicone oils, water such as degasified medium, and pasty highly viscous fluids. Prior to the treatment, this ultrasonic wave transmitting wave is filled in the hollow portion 6.

The clamping ring 31 is slidably mounted on the outer wall face of the tray 2, and by the sliding movement of the clamping ring 31, the casing 50 of the ultrasonic wave generator 100 is dismountably attached to the handle portion 3 of the tray 2, and it is sealed by the packing 30. In the drawings, reference numeral 150 represents an oscillator.

Figure 7:
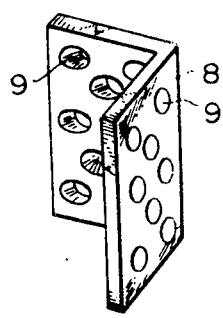
FIG. 7 is a diagram showing an example of the reflecting plate of the device of the present invention.
Figure 8:
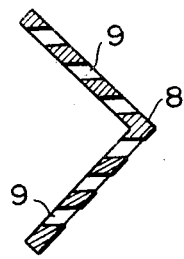
FIG. 8 is a sectional view of the reflecting plate shown in FIG. 7.

In the front in the radiation direction of ultrasonic waves from the top end of the horn 7, a reflecting plate 8 having a V-shaped section is disposed on the line connecting the horn 7 with the front tooth 10, so that ultrasonic waves radiated from the top end of the horn 7 and impinging against the surface of the reflecting plate change their directions to left and right. As shown in FIGS. 7 and 8, a great number of holes 9 are formed through the reflecting plate 8. Accordingly, ultrasonic waves which arrive at positions of the holes permeate through the reflecting plate 8 and are transmitted to the ultrasonic wave transmitting medium filled between the tray 2 and the front tooth 10 and perform an action of impregnating an active ingredient, such as tin fluoride, sodium fluoride or fluoroamine, of a tooth decay-retarding agent solution or paste coated on the surface of the front tooth 10, into the surface portion of the front tooth 10 to form a reinforcing layer thereon. Ultrasonic waves passing through upper holes 9 are reflected downwardly by a non-perforated reflecting plate 11 disposed above the front tooth 10 and radiated on the top face and back face of the front tooth 10. Ultrasonic waves reflected to left and right by the reflecting plate 8 are then reflected by a non-perforated reflecting plate 12 and radiated in directions parallel to lines of grinding teeth on both the left and right sides (see FIG. 4).

Figure 3:
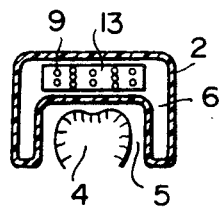
FIG. 3 is a view showing the section taken along the line I—I in FIG. 2.

Ultrasonic waves reflected by the lower portion of the non-perforated reflecting plate 12 arrive at the outer side face of the grinding tooth through the ultrasonic wave transmitting medium filled between the tray 2 and the tooth 4. Ultrasonic waves reflected by the upper portion of the reflecting plate 12 are transmitted substantially in parallel to the line of grinding teeth above the teeth 4, but since a reflecting plate 13 is disposed in the inclined state in the transmission passage of such ultrasonic waves (see FIG. 5) and holes 9 are formed through this reflecting plate 13 as shown in FIG. 3, parts of such ultrasonic waves are reflected downwardly while another parts of the ultrasonic waves advance straight.

As will be apparent from the foregoing illustration, by provision of the reflecting plate 8 having holes 9, ultrasonic waves radiated from the horn 7 of one ultrasonic wave generator 100 are not concentrated on front teeth 10 present in the front in the radiation direction but are dispersed, and they are radiated over a broad range to the front, top and back faces of all the teeth by actions of the non-perforated reflecting plates 11, 12 and 14 and the perforated reflecting plate 13. Accordingly, the treatment for forming a reinforcing layer of a tooth decay-retarding agent in the surface portions of teeth by radiation of ultrasonic waves to the surfaces of teeth in the presence the tooth decay-retarding agent can be accomplished effectively. Moreover, a vibrator capable of transmitting ultrasonic waves of a relatively low frequency, for example, about 500 KHz or lower, can be dismountably attached, and even a vibrator capable of transmitting ultrasonic waves of a frequency of 10 to 70 KHz giving optimum treatment results can be attached and the treatment can be performed effectively.

The reflecting plate is not limited to a perforated plane plate. For example, a very thin non-perforated metal plate acts as a transmitting member and simultaneously reflects parts of ultrasonic waves.

Figure 9:
FIGS. 9 to 12 are sectional views showing another examples of the reflecting plate of the device of the present invention.
Figure 10:
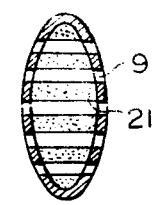
Figure 11:
Figure 12:
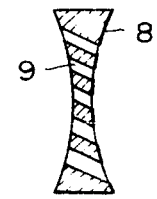

A suitable shape of the perforated plate can be chosen appropriately depending on the oject of the treatment among those shown in FIGS. 9, 11 and 12. In these examples, ultrasonic waves reflected from a concave surface are concentrated and act strongly on a limited area, while ultrasonic waves reflected from a convex surface expand in a broad area. In the example illustrated in FIG. 10, a material 21 incapable of transmitting ultrasonic waves, for example, foamed plastics, papers or felts, is filled in the interior of the reflecting plate-constituting material. In this case, the reflecting rate is improved.

Materials having a suitable rigidity, such as plastics and thin metal plates, are chosen for the reflecting material.

These reflecting plates may be attached to the inner wall face of the hollow portion 6 of the tray 2 according to known methods, for example, a method using a known adhesive, a soldering method and a method in which reflecting plates are engaged with engaging pieces formed on the inner wall face of the tray 2.

In the embodiments shown in the drawings, the horseshoe portion 1 of the tray 2 is formed to have a U-shaped section so that the tray 2 covers one of the upper and lower tooth rows. However, if the horseshoe portion 1 is formed to have an H-shaped section and grooves 5 are formed on the upper and lower portions, the tray 2 can cover both the upper and lower tooth rows and the treatment can be performed on teeth of both the upper and lower rows simultaneously.

Figure 2:
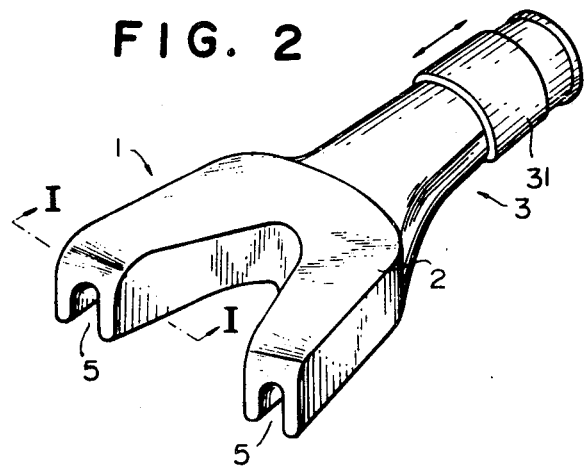
FIG. 2 is a perspective view of the device shown in FIG. 1.
Figure 4:
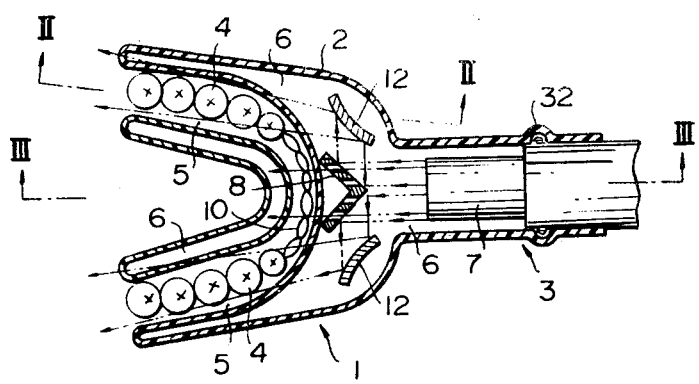
FIG. 4 is a view showing the plane taken along the line IV—IV in FIG. 5.
Figure 5:
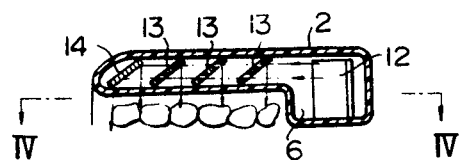
FIG. 5 is a view showing the section taken along the line II—II in FIG. 4.
Figure 6:
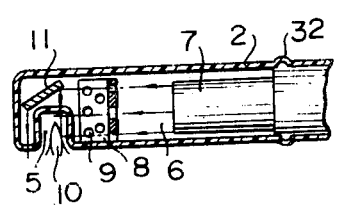
FIG. 6 is a view showing the section taken along the line III—III in FIG. 4.

The means for attaching the ultrasonic wave generator to the tray 2 and preventing leakage of the ultrasonic wave-transmitting medium filled in the tray 2 are not limited to those shown in FIGS. 1 and 2. For example, as illustrated in FIG. 4, a handle portion 3 is formed of a flexible material, a convex or concave fitting part 32 is formed on the handle portion 3, and a concave or convex part is formed on the corresponding portion of the ultrasonic wave generator, for example, on the casing 50. Also by this arrangement, leakage of the ultrasonic wave transmitting medium can be prevented completely and the ultrasonic wave generator can be attached assuredly. In addition, as will be apparent to those skilled in the art, there can be adopted methods using known connecting means, for example, a method in which a connecting tube is used for attaching the ultrasonic wave generator to the tray through screws, though specifically illustrated in the drawings.

Further, the ultrasonic wave generator is not limited to the horn attached to the magnetostriction vibrator specifically illustrated in the drawings. Known electrostriction vibrators such as a barium titanate porcelain and a lead zircotitanate (PZT) porcelain and known piezoelectric vibrators such as quartz can be used appropriately according to need.

In connection with the reflection of ultrasonic waves, which constitutes the basic technical concept of the present invention, we made experiments and investigations such as mentioned below, and it was confirmed that ultrasonic waves which have been reflected have the substantially same tooth decay-retarding treatment effect as that of ultrasonic waves which are not reflected.

Figure 13:
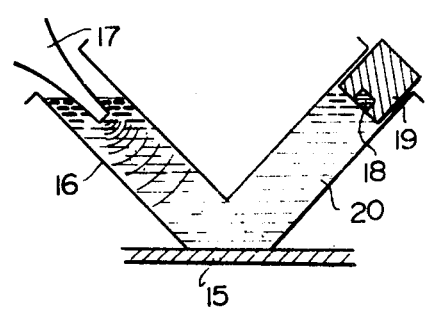
FIG. 13-(a) is a diagram illustrating the experiment for determining reflecting effects.
Figure 13:
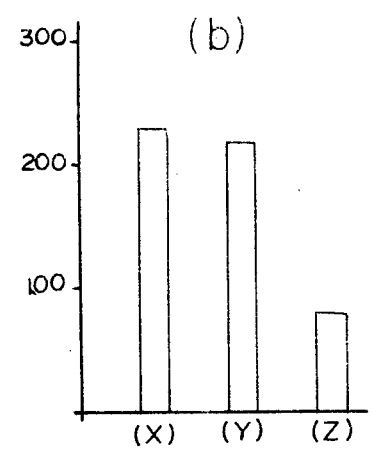

More specifically, as illustrated in FIG. 13-(a), a stainless steel reflecting plate 15 having a thickness of 0.2 mm was attached to a V-shaped combined cylinder 16 having a length of 7.5 cm, and a horn 17 of a ultrasonic wave generator 17 was inserted from one end of the cylinder 16 and a sample prepared by embedding an enamel piece 18 formed from a human tooth into a resin 19 was attached to the other end of the cylinder 16. An 8% aqueous solution 20 of tin fluoride was filled in the cylinder 16 and ultrasonic waves having a frequency of 28 KHz were radiated from the horn 3 for 20 seconds. Then, the surface of the sample was brush-washed and dipped in an acetic acid buffer solution having a concentration of 0.1 mole/l for 2 hours to effect deliming. Then, the Vickers hardness of the sample was measured. Obtained results are shown in FIG. 13-(b). As is seen from FIG. 13-(b), the effect (Y) attained by the above treatment is substantially the same as the effect (X) attained by direct radiation of ultrasonic waves and is much higher than the effect (Z) obtained when radiation of ultrasonic waves was not conducted.

The device of the present invention guarantees that teeth of a broad range can be treated with the substantially same sonic pressure of ultrasonic waves. Further, ultrasonic waves of a low frequency region having a higher treatment effect can be conveniently utilized if the device of the present invention is used. Since ultrasonic waves can be reflected and allowed to advance straight only by provision of one perforated reflecting plate, the structure of the device can be remarkably simplified. The ratio of reflected ultrasonic waves and those advancing straight can optionally be chosen by the manner of forming holes or the selection of the plate thickness. Therefore, such disadvantages as a pain to a patient by an excessive sonic pressure and an insufficient effect on a grinding tooth or the like by an insufficient sonic pressure can be eliminated. Still further, the degree of concentration or divergency of ultrasonic waves can be appropriately adjusted by adjusting the curvature of the surface of the reflecting plate. These are advantages attained by the present invention.

Thus, it will be seen that the invention provides a device for forming a reinforcing layer of a tooth decay-retarding agent on the surface portion of a tooth by radiation of ultrasonic waves to the surface of the tooth in the presence of the tooth decay-retarding agent, which comprises a reflecting plate for reflecting ultrasonic waves emitted from a ultrasonic wave generator, said reflecting plate being capable of reflecting a part of the ultrasonic waves and allowing another part of the ultrasonic waves to pass therethrough and said reflecting plate being disposed at a certain angle to the radiation direction of the ultrasonic waves.

When the device of the present invention is used, teeth a broad range can be treated with the substantially same sonic pressure of ultrasonic waves. Further, ultrasonic waves of low frequency region having a higher treatment effect can be conveniently utilized. Since ultrasonic waves can be reflected and allowed to advance straight only by provision of one perforated reflecting plate, the structure of the device can be remarkably simplified. The ratio of reflected ultrasonic waves and those advancing straight can optionally be chosen by the manner of forming holes or the selection of the plate thickness. Therefore, such disadvantages as a pain to a patient by an excessive sonic pressure and an insufficient effect on a grinding tooth or the like by an insufficient sonic pressure can be eliminated. Still further, the degree of concentration or diveagency of ultrasonic waves can be appropriatedly adjusted by adjusting the curvature of the surface of the reflecting plate.

It is thus apparent that the structure of the invention includes a support means 1, which is formed by the hollow body constituting the tray 2. This support means carries the plate 8 shown in FIGS. 7 and 8 and forming a reflecting-and-transmitting plate means to receive the waves from the generating means 50. Part of the waves are transmitted through the plate means 8 directly to the teeth situated at the side thereof opposite from the generating means 50, while another part of the transmitted waves travel through a portion of the plate means 8 which is situated beyond the teeth to the reflecting plate means 11 which is inclined in the manner shown in FIG. 6 to direct waves downwardly toward the teeth 10 for treating the edges and rear surfaces thereof. The reflecting plate means 12 are carried by the support means on opposite sides of the plate means 8 to receive the waves reflected thereby and to further reflect the waves to the plurality of inclined plate means 13 which are respectively carried by elongated portions of the support means formed by the tray 2. All of these plate means 13 are also reflecting-and-transmitting plate means so that part of the waves from one of the pair of reflecting plate means 12 are reflected to the teeth which are in line with the several plates 13 while other waves are transmitted through these plates. Thus the plate 13 which is nearest to one of the plates 12 reflects part of the waves received therefrom and transmits the remainder of the waves to the next plate 13 which in turn reflects part of the waves and transmits the remainder to the following plate 13, while in the illustrated example this third plate 13 reflects part of the waves and transmits the remainder to the plate 14 which is most distant from the plate 12 and which is impermeable to the waves so that this last plate 14 serves only to reflect the waves to the teeth which are most distant from the particular reflecting plate means 12.

Since the reflecting-and-transmitting plate means 8 is of the illustrated V-shaped configuration, although it may also have a U-shaped configuration, it is clear that this plate means 8 has a central portion nearest to the generating means 50 and a pair of opposed side edge portions most distant therefrom with the plate means 8 having between its central and free side edge portions reflecting surfaces for respectively reflecting the waves

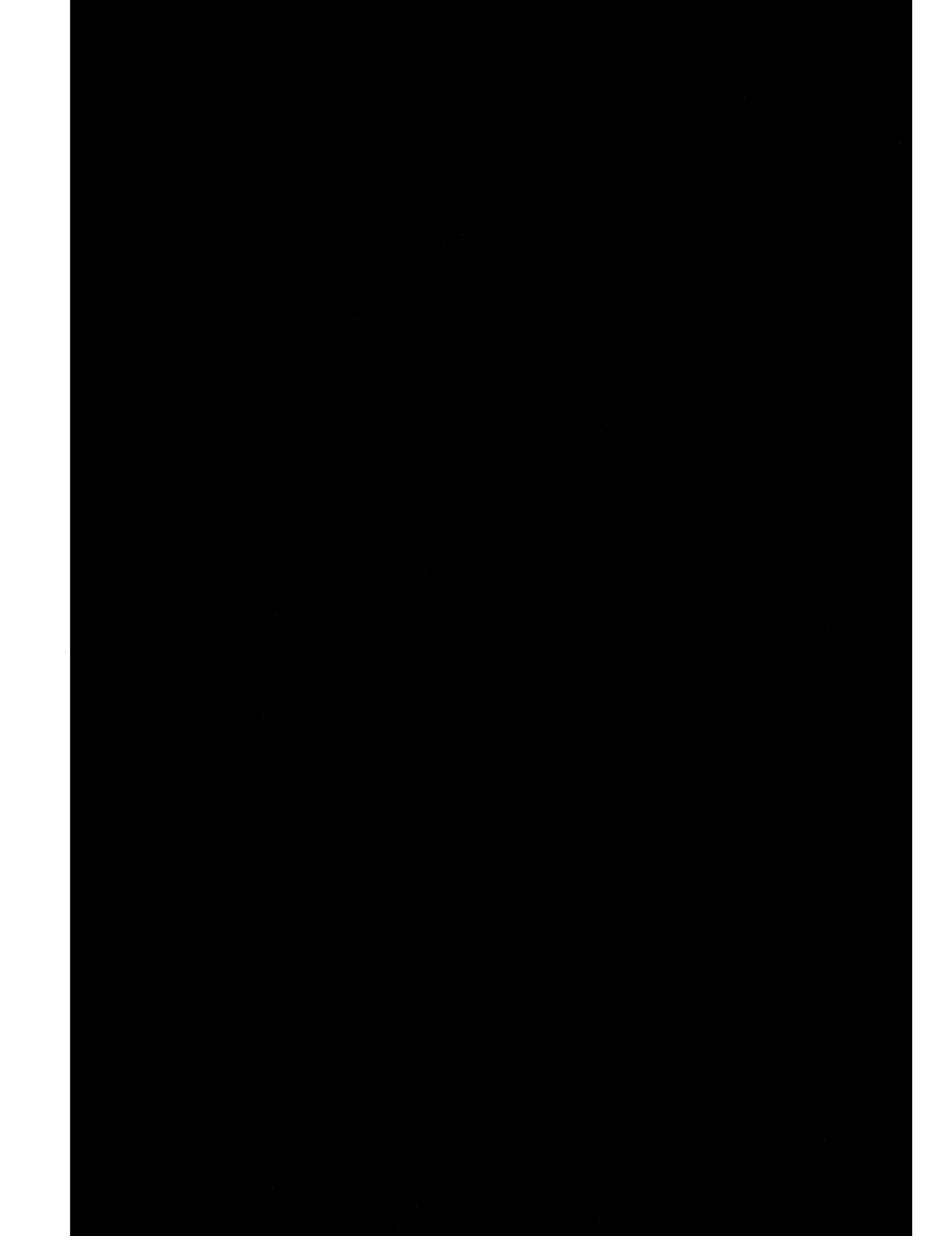

15. The combination of claim 12 and wherein said plate means are adapted to extend beyond the teeth situated at the side of said plate means opposite from said generating means, so that part of the waves transmitted through said plate means travel beyond edges of the teeth at the side of said plate means opposite from said generating means, and said support means carrying at the side of said plate mean opposite from said generating means adapted to be in line with the teeth situated at the side of the latter plate means opposite from said generating means a reflecting plate means which is impermeable to said waves while capable of reflecting the latter, and said reflecting plate means being situated in the path of the waves which travel through said reflecting-and-transmitting plate means to receive the part of the transmitted waves which travel beyond the teeth situated at the side of said reflecting-and-transmitting plate means opposite from said generating means, said reflecting plate means which is totally impermeable to the waves having a surface which is inclined for receiving and reflecting to the teeth the waves which travel through that part of said reflecting-and-transmitting plate means which are adapted to extend beyond the teeth, whereby through the reflecting plate means which is totally impermeable to the waves some of the waves can be directed toward the edges and rear surfaces of the teeth.

* * * * *